United States Patent [19]
Willis

[11] Patent Number: 5,820,568
[45] Date of Patent: Oct. 13, 1998

[54] APPARATUS AND METHOD FOR AIDING IN THE POSITIONING OF A CATHETER

[75] Inventor: Nathaniel Parker Willis, Atherton, Calif.

[73] Assignee: Cardiac Pathways Corporation, Sunnyvale, Calif.

[21] Appl. No.: 732,511

[22] Filed: Oct. 15, 1996

[51] Int. Cl.⁶ .................................................. A61B 5/0402
[52] U.S. Cl. .......................................... 600/523; 600/509
[58] Field of Search ..................................... 128/639, 642, 128/898, 696, 710, 712; 607/98, 99, 101, 102, 122; 600/372, 373, 374, 509, 523, 525

[56] References Cited

U.S. PATENT DOCUMENTS

| | | | |
|---|---|---|---|
| 4,522,212 | 6/1985 | Gelinas et al. | 128/642 |
| 4,699,147 | 10/1987 | Chilson et al. | 128/642 |
| 5,156,151 | 10/1992 | Imran | 128/642 |
| 5,228,442 | 7/1993 | Imran | 128/642 |
| 5,237,996 | 8/1993 | Waldman et al. | 128/642 |
| 5,279,299 | 1/1994 | Imran | 128/642 |
| 5,324,284 | 6/1994 | Imran | 606/15 |
| 5,341,807 | 8/1994 | Nardella | 128/642 |
| 5,342,295 | 8/1994 | Imran | 604/43 |
| 5,357,979 | 10/1994 | Imran | 128/772 |
| 5,391,147 | 2/1995 | Imran et al. | 604/95 |
| 5,397,339 | 3/1995 | Desai | 607/116 |
| 5,400,783 | 3/1995 | Pomeranz et al. | 128/642 |
| 5,411,025 | 5/1995 | Webster, Jr. | 128/642 |
| 5,465,717 | 11/1995 | Imran et al. | 128/642 |
| 5,469,857 | 11/1995 | Laurent et al. | 128/710 |
| 5,476,495 | 12/1995 | Kordis et al. | 607/122 |
| 5,598,848 | 2/1997 | Swanson et al. | 128/642 |

OTHER PUBLICATIONS

"Endocardial Activation Mapping and Endocardial Pace–Mapping using a Balloon Apparatus"—James I. Fann, BS, et al., The American Journal of Cardiology, vol. 55, Apr. 1, 1985, pp. 1076–1083.

Endocardial Mapping by Simultaneous Recording of Endocardial Electrograms During Cardiac Surgery for Ventricular Aneurysm, Jacques M.T. de Bakker, MSc, et al., JACC vol. 2 No. 5, Nov. 1983: pp. 947–953.

"The Detection of Unipolar and Bipolar Cardiac Electrograms with a Movable Coaxial Electrode", Howard C. Hughes, et al., Journal of Surgical Research, vol. 31, No. 6, Dec. 1981, pp. 469–474.

*Primary Examiner*—George Manuel
*Assistant Examiner*—Kennedy J. Schaetzle
*Attorney, Agent, or Firm*—Limbach & Limbach L.L.P.

[57] ABSTRACT

A system for aiding in the positioning of a catheter. The system includes a basket shaped catheter having a plurality of bipoles arranged thereon for sensing voltage potentials generated by tissue. An analog to digital converter is coupled to the catheter and configured to convert the sensed voltage potentials to digital signals. A computer is coupled to the analog to digital converter and to a video display and is programmed to calculate an absolute value of a slope of each of the digital signals. The computer is also programmed to generate and display on the video display a graphical representation of the absolute values of the slopes on a first image corresponding to the catheter. A method of aiding in the positioning of a catheter against a tissue surface is also disclosed.

60 Claims, 14 Drawing Sheets

APPARATUS AND METHOD FOR AIDING IN THE POSITIONING OF A CATHETER

BACKGROUND OF THE INVENTION

1. Field of the Invention

The present invention relates to cardiac mapping catheters and, in particular, to an apparatus and method for aiding in the positioning of such catheters.

2. Description of the Related Art

Electrophysiology is a specialty within the field of cardiology for diagnosis and treatment of electrical abnormalities of the heart. Diagnosis is performed using electrode-bearing catheters placed within the heart chambers. Electrical abnormalities are typically diagnosed by detecting the course of electrical activation paths along the endocardial surfaces of the heart chambers over time. To do this, the cardiologist may place one or more electrode-bearing catheters within a chamber of the heart to get a better "picture" of this electrical activity.

Sometimes the electrical activity is cyclical, i.e., repeats fairly well from heartbeat to heartbeat. Examples include atrial flutter and ventricular tachycardia. In such cases, a catheter having few electrodes may serve to perform the diagnosis by moving the electrodes to various regions and then performing a point-by-point comparison of activation times with a reference. This reference may be an external EKG or another electrode catheter maintained in a stable position within a heart chamber.

However, certain types of electrical activity within a heart chamber are not cyclical. An example includes atrial fibrillation. Such electrical activity is random from beat to beat. To analyze or "map" this type of electrical activity, the "picture" must be obtained during one beat. In other words, all the points of the map or picture must be obtained simultaneously within one-tenth of a second. Mapping of electrical activity in a single beat for cyclic arrhythmias is advantageous because it dramatically reduces procedure time and it allows for mapping of hemodynamically unstable arrhythmias.

Cardiac mapping is a method by which potentials recorded directly from a heart are spatially depicted as a function of time in an integrated manner. Electrodes are utilized for recording potentials at different positions on the endocardial wall of a heart chamber, such as the ventricle, so that various and important electrophysiological variables can be identified from the cardiac recordings. Such variables include local activation times, waveform morphology, and potential distribution during depolarization and repolarization. Cardiac mapping is very important in locating abnormal foci in the heart and the mapping probe may even be utilized in destroying such foci.

Cardiac mapping is preferably performed in an endocardial manner, i.e., within an interior chamber wall or endocardial wall in the heart. Referring to FIG. 1, one way of carrying out such mapping is with a cardiovascular catheter 20 having a retractable basket-shaped electrode array. Examples of such basket-shaped electrode array catheters are disclosed in U.S. Pat. Nos. 4,699,147 to Chilson et al., 5,411,025 to Webster, Jr., and 5,465,717 to Imran et al., the contents of each being hereby fully incorporated into the present application by reference.

The retractable basket-shaped electrode array of the catheter 20 is formed by a plurality of arms 22 with each arm supporting a plurality of spaced-apart electrode pairs 24, or bipoles 24. Specifically, the catheter 20 includes five arms 22 with each arm carrying four bipoles 24. There are five output wires 26, one for each of the five arms 22, and each output wire 26 includes eight conductors, two for each of the bipoles 24. Each of the bipoles 24 detects a cardiac electrogram (EGM) signal which is carried by two conductors in one of the output wires 26. Because the catheter 20 is able to hold a large number of electrodes, it is often referred to as a high density mapping catheter.

Referring to FIG. 2, the catheter 20 is able to hold its electrodes in different relative positions within a heart chamber 28. By this means, the cardiologist can obtain a map of electrical activity in one heartbeat by recording electrical signals from all the electrodes simultaneously. This is done by analyzing the spatial and temporal relationship of the electrical signals received at the electrodes.

By rotating the catheter 20 and/or moving it longitudinally and recording electrical signals, a series of maps or pictures can be produced. A series of such pictures is often able to better define the ectopic sites of activation or other activation pathways that contribute to the malfunction. This type of information may then allow the cardiologist to intervene with another catheter to destroy that causative tissue. Such destruction of heart tissue is referred to as "ablation," which is a rapidly growing field within electrophysiology and obviates the need for maximally invasive open heart surgery.

When recording the signals from electrophysiology catheters, contact of the catheter electrodes with the endocardial surface is desirable. However, it is common for high density mapping catheters, such as the catheter 20, to not have 100% of their electrodes in contact with the endocardium. If the electrodes are not in contact, recorded signals have low amplitude because they are farther away from the endocardial surface. In addition, the recorded signal is less specific because the electrodes sense from a larger portion of the endocardial surface. This, in turn, imparts a high degree of uncertainty or error in any map of electrical activity produced with the electrodes not fully in contact with the endocardial surface. When the electrodes are in contact with the surface, the recorded signal is dominated by the portion of tissue directly under the recording electrodes, resulting in more specific information about electrical activity in this tissue.

The degree of contact between the electrodes of a catheter having relatively few electrodes, i.e., not a catheter having a basket-shaped electrode array like the catheter 20, and the endocardial surface has typically been determined by one or more of the following techniques: 1) catheter position as seen on a fluoroscope; 2) catheter steering feedback; 3) signal content; and/or 4) pacing thresholds. Using a fluoroscope to determine catheter position is relatively self explanatory. Catheter steering feedback is a process of feeling when the catheter encounters a barrier, such as the endocardial wall. Using the signal content to determine contact is possible because the signal content is normally dependent on the quality of electrode contact. Finally, a pacing threshold is the amount of current which is required to be fed into one of the electrodes in order to "capture" the heart, i.e., causes the heart to pace. In general, the lower the pacing threshold (i.e., the lower the current), the better the contact.

Determination of electrode contact with high density mapping catheters that have many electrodes, such as the catheter 20, is much more difficult. The techniques used for catheters with relatively few electrodes are not necessarily applicable to high density mapping catheters. With respect to fluoroscopic imaging, the complex structure of high density mapping catheters means that the overall shape or position of the catheter does not always reveal accurate information about electrode contact. With respect to catheter steering feedback, the distributed structure of the high density mapping catheter makes it difficult to feel whether individual arms of the catheter are encountering barriers. The large number of electrodes on high density mapping catheters makes visual inspection of signals and calculation of pacing thresholds too time consuming for practical application in every case. Usually, the clinician wants immediate feedback on electrode contact.

When the electrodes have poor contact, there is a high degree of uncertainty introduced into the results of the mapping procedure. If the clinician had an efficient way to determine during the mapping procedure whether or not electrodes are in contact, it would be a significant time saver. Therefore, because it is desirable for high density mapping catheters to be deployed and positioned with their electrodes in contact with the endocardial surface, there is a need for an apparatus and method for aiding a cardiologist in the positioning of such catheters.

SUMMARY OF THE INVENTION

The present invention is a system for aiding in the positioning of a catheter, having at least one electrode thereon, against a tissue surface. The system includes monitoring means, processing means, a video display and graphics generation means. The monitoring means monitors a voltage potential sensed by the electrode on the tissue surface. The processing means processes the voltage potential to evaluate a degree of contact between the electrode and the tissue surface and generates a contact signal representative of the degree of contact. The graphics generation means is responsive to the contact signal and generates and displays on the video display a graphical representation of the degree of contact.

Another embodiment of the present invention is a system for aiding in the positioning of a catheter. The system includes a catheter, processing means, a video display and graphics generation means. The catheter has at least one electrode thereon for sensing a voltage potential on a tissue surface. The processing means processes the voltage potential to evaluate a degree of contact between the electrode and the tissue surface and generates a contact signal representative of the degree of contact. The graphics generation means is responsive to the contact signal and generates and displays on the video display a graphical representation of the degree of contact.

Another embodiment of the present invention is a system for aiding in the positioning of a catheter. The system includes a catheter, a video display and a computer. The catheter has at least one electrode thereon for sensing a voltage potential on a tissue surface. The computer is coupled to the catheter and to the video display and is programmed to process the voltage potential to evaluate a degree of contact between the electrode and the tissue surface. The computer is also programmed to generate and display on the video display a graphical representation of the degree of contact on a first image corresponding to the catheter.

Another embodiment of the present invention is a method of aiding in the positioning of a catheter, having at least one electrode thereon, against a tissue surface. The method includes the steps of: monitoring a voltage potential sensed on the tissue surface by the electrode; processing the voltage potential to evaluate a degree of contact between the electrode and the tissue surface; generating a graphical representation of the degree of contact on a first image corresponding to the catheter; and displaying the graphical representation and the first image on a video display.

A better understanding of the features and advantages of the present invention will be obtained by reference to the following detailed description of the invention and accompanying drawings which set forth an illustrative embodiment in which the principles of the invention are utilized.

DETAILED DESCRIPTION OF THE INVENTION

Figures 1, 2:
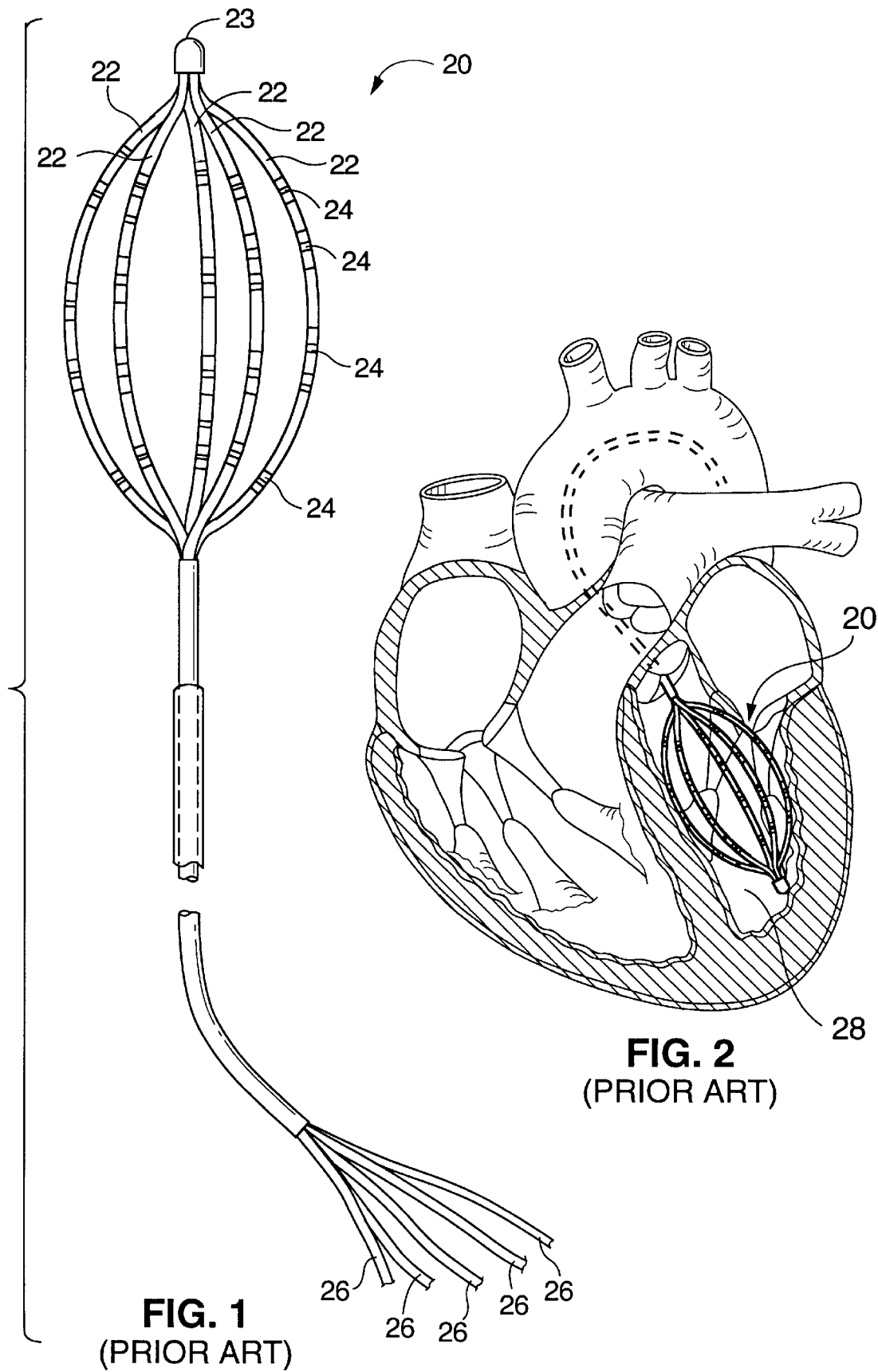
FIG. 1 is an isometric view illustrating a conventional basket shaped endocardial catheter.
FIG. 2 is a cross-sectional view of a human heart illustrating the positioning of the catheter shown in FIG. 1.
Figure 3:
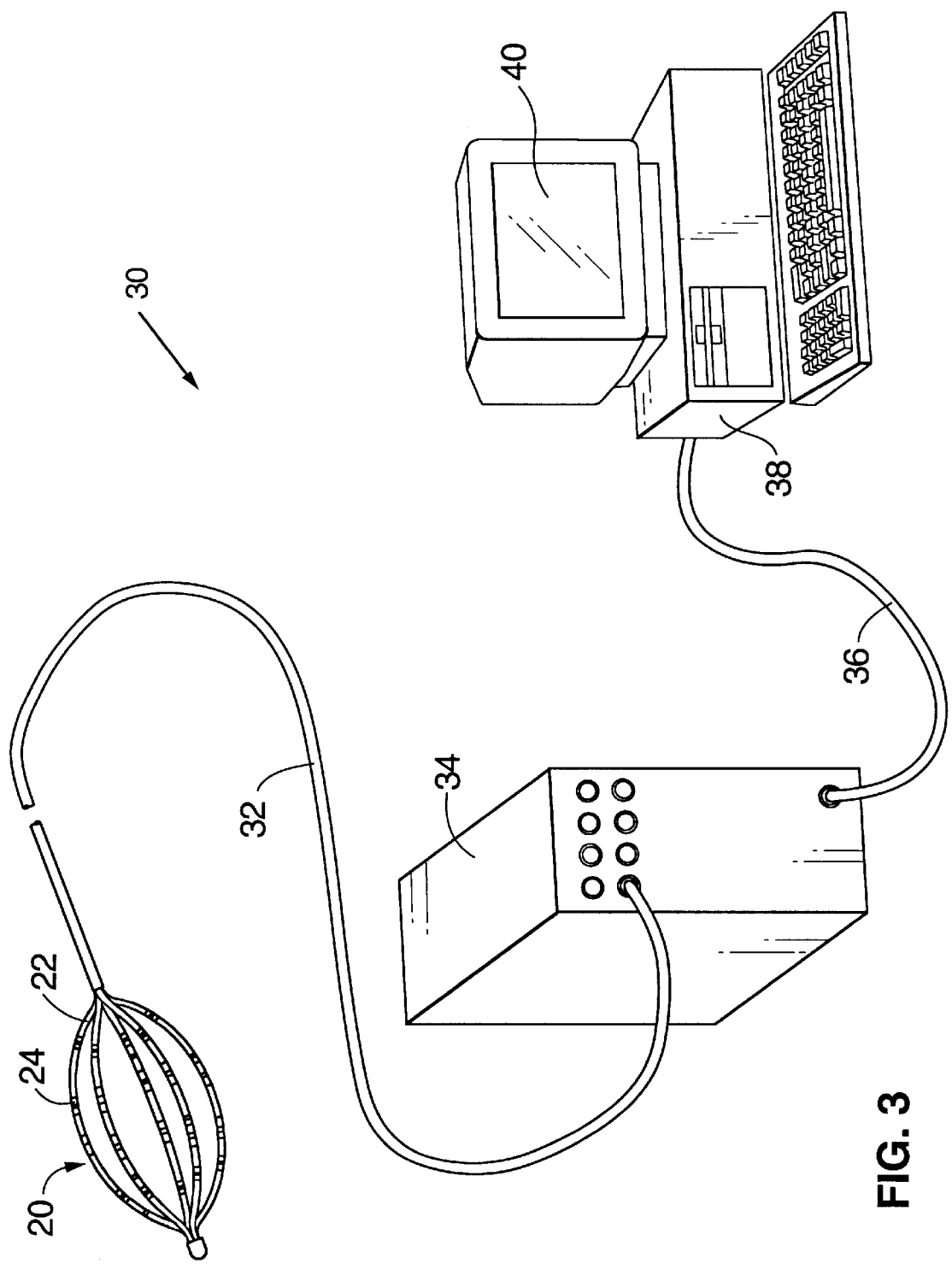
FIG. 3 is a pictorial illustration of a system in accordance with the present invention.

Referring to FIG. 3, there is illustrated a positioning system 30 in accordance with the present invention. The system 30 provides electrode contact information to the clinician during the deployment and positioning process of the catheter 20. The contact information is fed back to the clinician in real time. This real-time feedback allows the clinician to interactively adjust the deployment of the catheter 20 to optimize electrode contact. It is envisioned that the importance of feeding back contact information in real time will increase as additional steering capabilities are integrated into high density mapping devices.

The system 30 includes the catheter 20, a cable 32 connecting the catheter 20 to an amplifier 34, and another cable 36 connecting the amplifier 34 to the I/O card of a computer 38. A display 40 displays information processed by the computer 38. In general, the system 30 uses the content of the EGM signals detected by the electrode bipoles of the catheter 20 to provide real-time electrode contact feedback to the clinician in the form of a graphical representation of the catheter 20 on the display 40. The computer 38 processes the EGM signals to evaluate or estimate the level, or degree, of contact between the electrodes and the endocardial tissue surface. In order to perform such processing, the computer 38 executes an algorithm implemented in software. The output of the algorithm for the EGM signal detected by each bipole of the catheter 20 is presented to the clinician in a real-time graphical output on the display 40.

Although the embodiment of the positioning system 30 described herein provides contact information for a catheter having a basket-shaped electrode array, such as the catheter 20, it should be well understood that the teachings of the present invention may be applied to other types of catheters having virtually any shape and configuration. Furthermore, basket-shaped catheters can have many different configurations. For example, the catheter 20 includes five arms 22 and is considered a sector basket which is used for higher density localized mapping. In contrast, a full chamber basket may include eight arms. The present invention is also not limited to catheters using bipoles, or electrode pairs, but rather, it is believed that the teachings of the present invention may be applied to single electrodes, or unipoles, as well.

Figure 4:
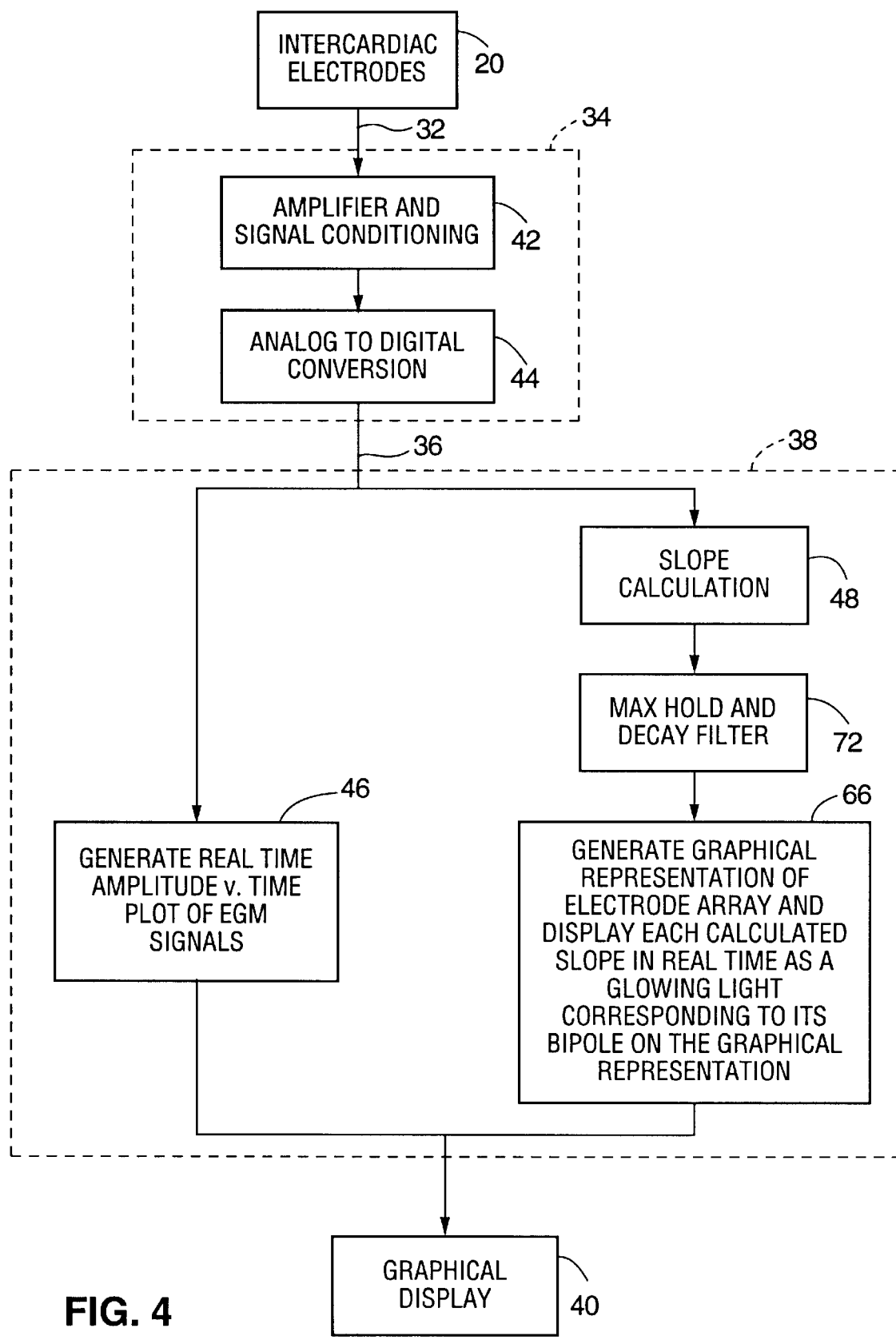
FIG. 4 is a flow diagram illustrating the operation of the system shown in FIG. 3.

The operation of the system 30 can be described by referring to the data flow diagram shown in FIG. 4. The EGM signals detected by the bipoles of the catheter 20 are carried by the cable 32 to the amplifier 34. The catheter 20 as shown in the drawings includes five arms 22 with four bipoles 24 on each arm for a total of twenty bipoles. Thus, twenty EGM signals are carried and kept separate from each other by the cable 32. It should be well understood, however, that the catheters used with the present invention may have any number of electrodes and may have any configuration.

The amplifier 34 amplifies and conditions the EGM signals in block 42 and converts the analog EGM signals to digital signals in block 44.

Figure 5:
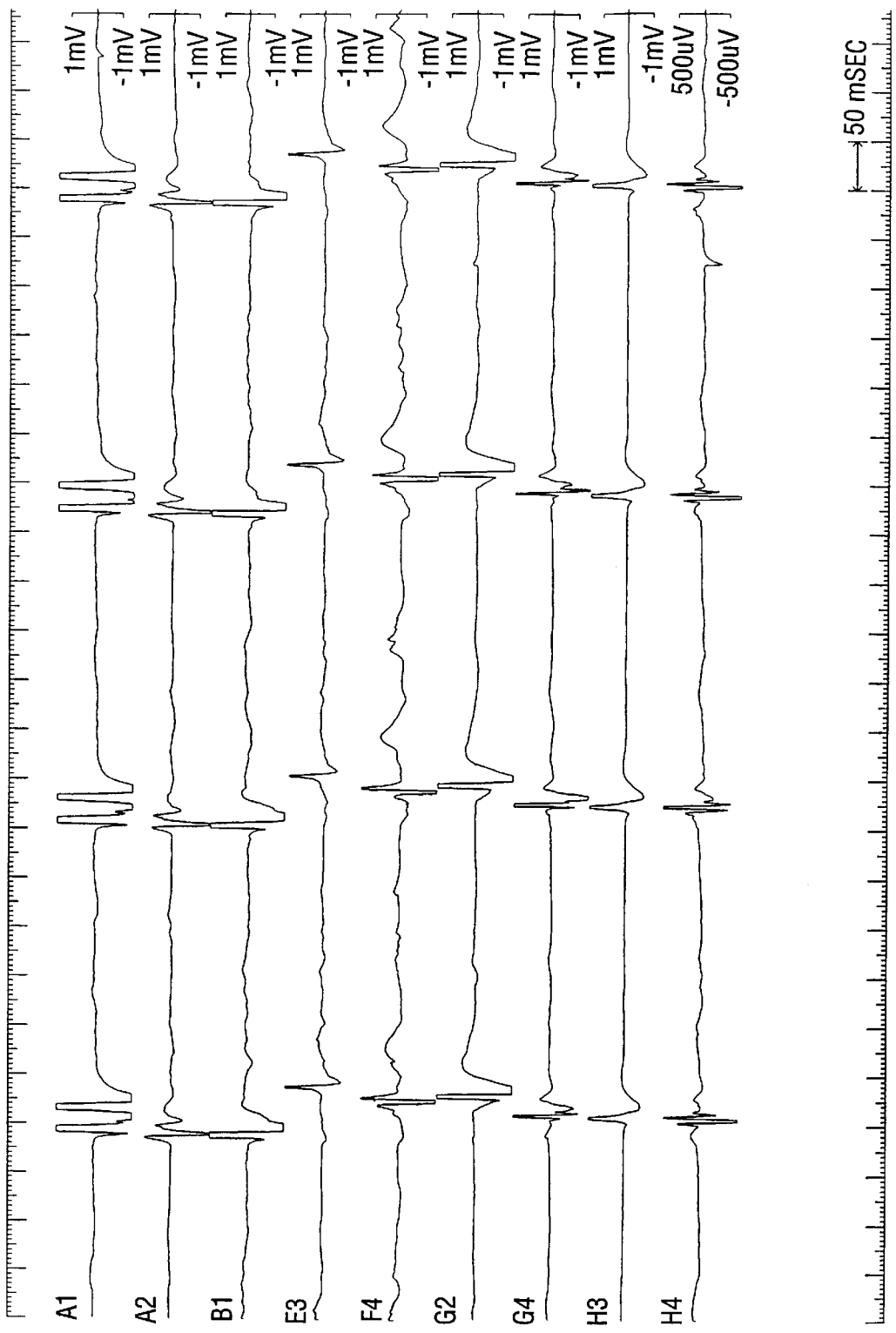
FIGS. 5, 6 and 7 are amplitude versus time plots of EGM signals sensed by an endocardial basket catheter.
Figure 6:
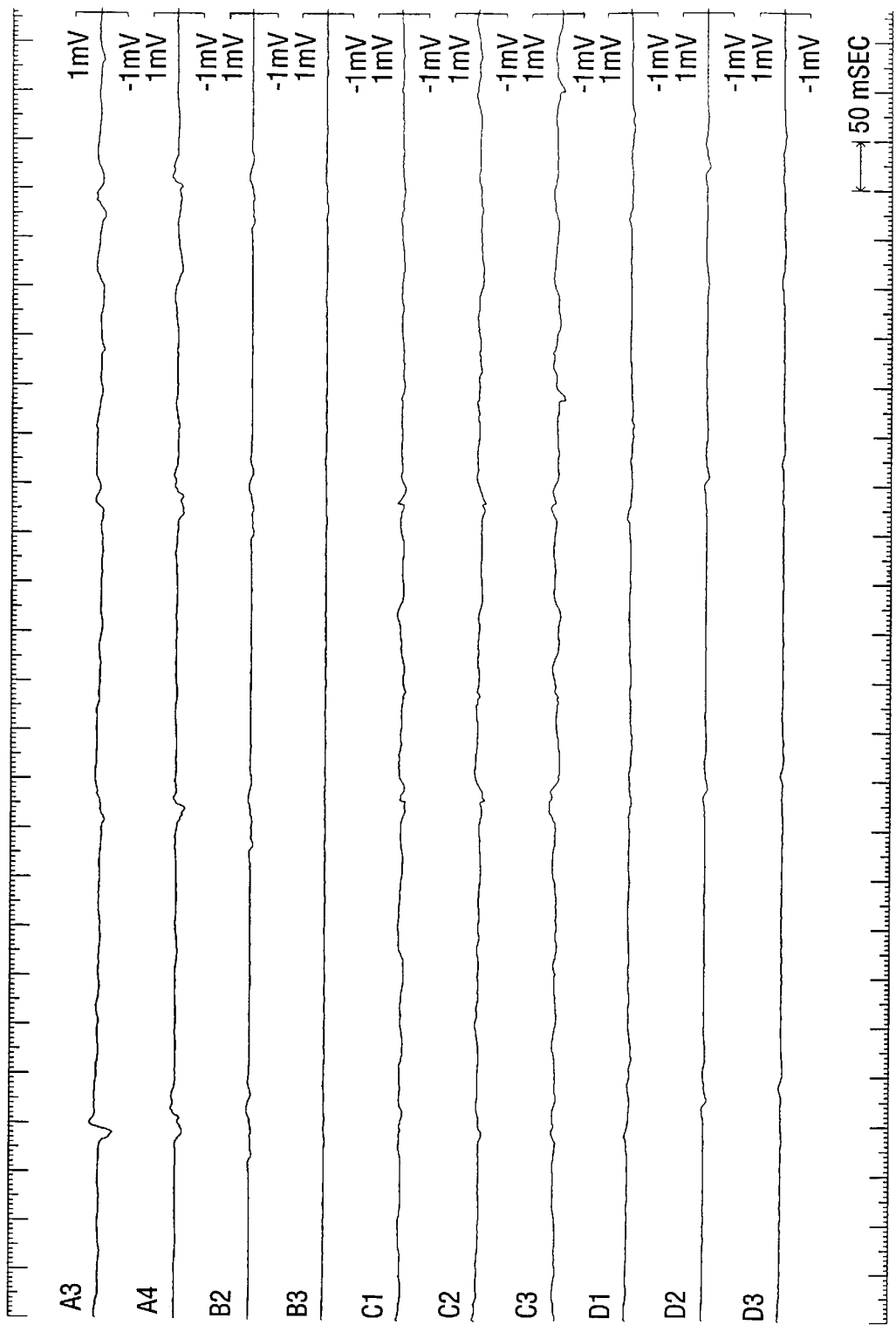
Figure 7:
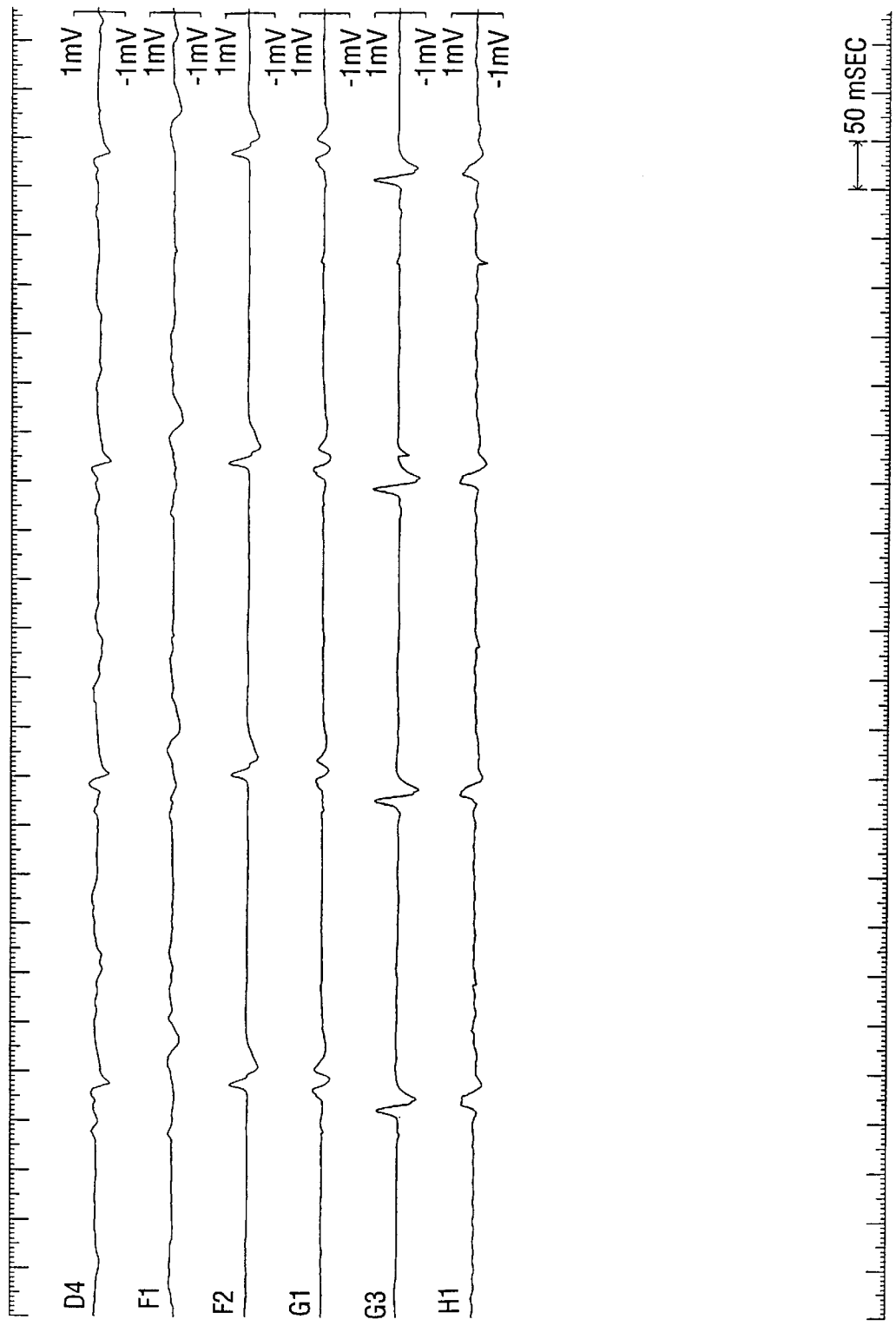

The cable 36 carries the digital EGM signals to the I/O card of the computer 38. The computer 38 processes the digital EGM signals in real time and generates output data for viewing on the display 40. The output data shown on the display 40 provides electrode contact information to the clinician during the deployment and positioning process of the catheter 20. The output data may be displayed in many different forms. For example, as shown in block 46, the computer 38 may generate an amplitude versus time plot of each EGM signal. This results in the actual EGM signal detected by each bipole being shown on the display 40 in real time, as is illustrated in FIGS. 5, 6 and 7. FIGS. 5, 6 and 7 each show several bipolar signals recorded from a high density mapping catheter located in the left ventricle of a human patient during ventricular tachycardia.

In order to assess the quality, or degree, of the contact between the electrodes of the catheter 20 and the endocardial surface, the content of each of the EGM signals detected by the electrodes is analyzed. For example, the activation component of the bipolar EGM signals can be examined to assess contact. If the activation is "fast", then the signal is considered to be in contact. The term "fast" refers to a rapid deflection during activation. A rapid deflection implies activations with steep slope and short duration. In contrast, bipolar signals recorded from electrodes that are not in contact are referred to as "slow". Such "slow" signals tend to have slowly deflecting, smaller amplitude, wider duration pulses during activation. "Slow" signals also tend to have more gradual slopes.

FIG. 5 shows EGM signals recorded from electrode bipoles that were positioned such that they paced the heart when 2 mA of current was fed into them, i.e., the bipoles had a 2 mA pacing threshold. FIGS. 6 and 7 show EGM signals recorded from electrode bipoles that were positioned such that they did not pace the heart when 5 mA of current was fed into them, i.e., the bipoles had a pacing threshold greater than 5 mA. Based on pacing thresholds, one would classify the electrodes which detected the signals shown in FIG. 5 as in contact and the electrodes which detected the signals shown in FIGS. 6 and 7 as not in contact. The "fast" and "slow" characteristics of the signals shown in FIG. 5 and FIGS. 6 and 7, respectively, is clearly visible.

The "fast" or "slow" character of the EGM signals is a heuristic evaluation of the activation component of the signal. A better way to evaluate the EGM signals would be to use an algorithm which determines the degree of contact. One way to develop such a contact algorithm is to determine mathematical parameters that quantify the heuristic. In other words, one or more specific parameters of the EGM signals are chosen and analyzed to assess electrode contact. One possible parameter is the amplitude of the EGM signal. Analyzing the amplitude, however, is probably not the most effective way to determine contact because the amplitude of a bipole has a directional dependence that is independent of electrode contact.

The slope of a bipolar EGM signal, on the other hand, is equivalent to the rate of deflection and therefore is a good measure of the "fast" or "slow" nature of the signals. Therefore, the system 30 assesses the quality of the electrode contact by calculating the slope of activation of the EGM signals. It should be well understood, however, that many different parameters included in the EGM signals could be analyzed in order to assess the quality of the contact between the electrodes and the endocardial surface in accordance with the present invention. For example, other possible parameters include: 1) the slope divided by the peak-to-peak amplitude of activation; and 2) the slope multiplied by the peak-to-peak amplitude.

There is no significant additional information in the sign of the slope of a bipolar EGM signal. The sign is arbitrary and only depends on how the leads are connected to the differential amplifier that is recording the EGM signal from the electrode. Therefore, the data can be simplified without any loss of information by taking the absolute value of the slope.

Figure 8:
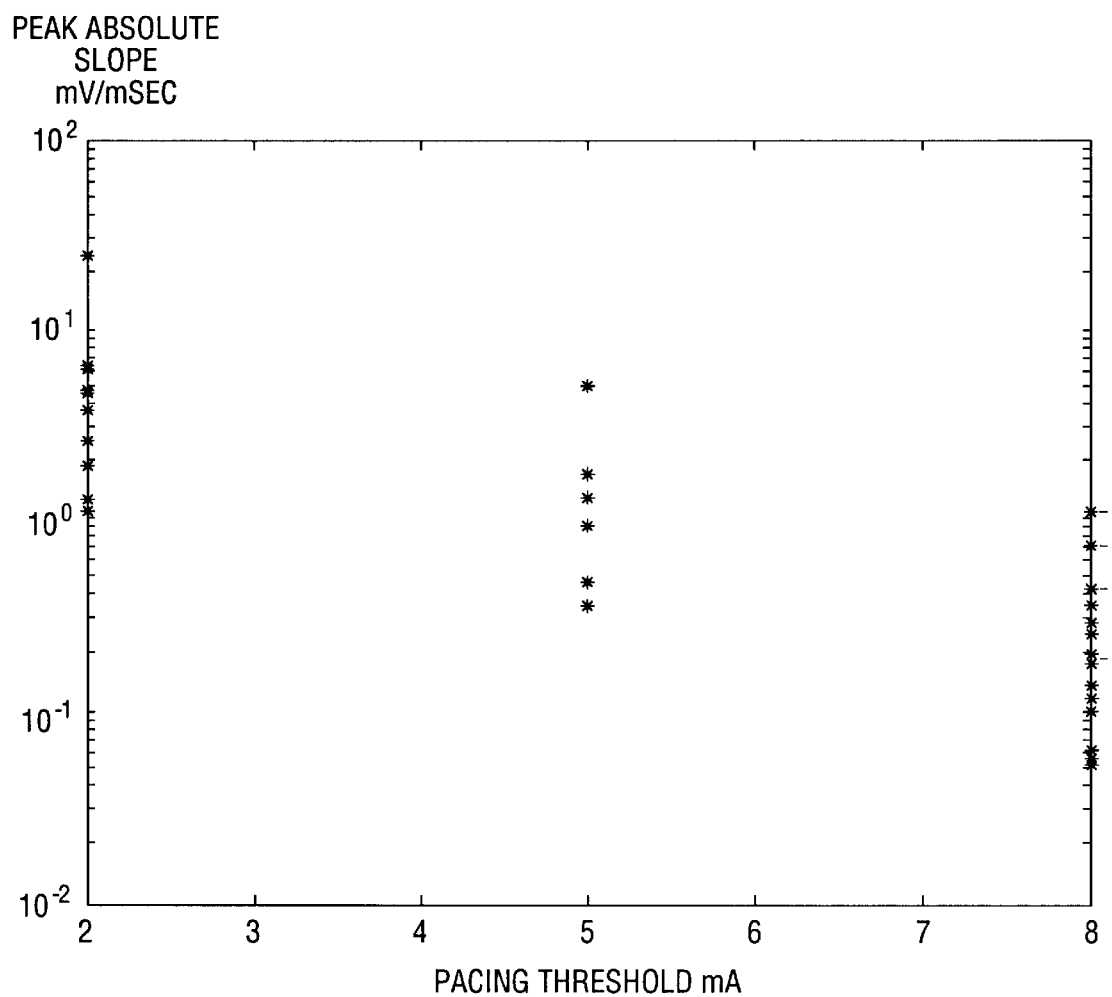
FIGS. 8 and 9 are plots of pacing threshold versus peak absolute slope.
Figure 9:
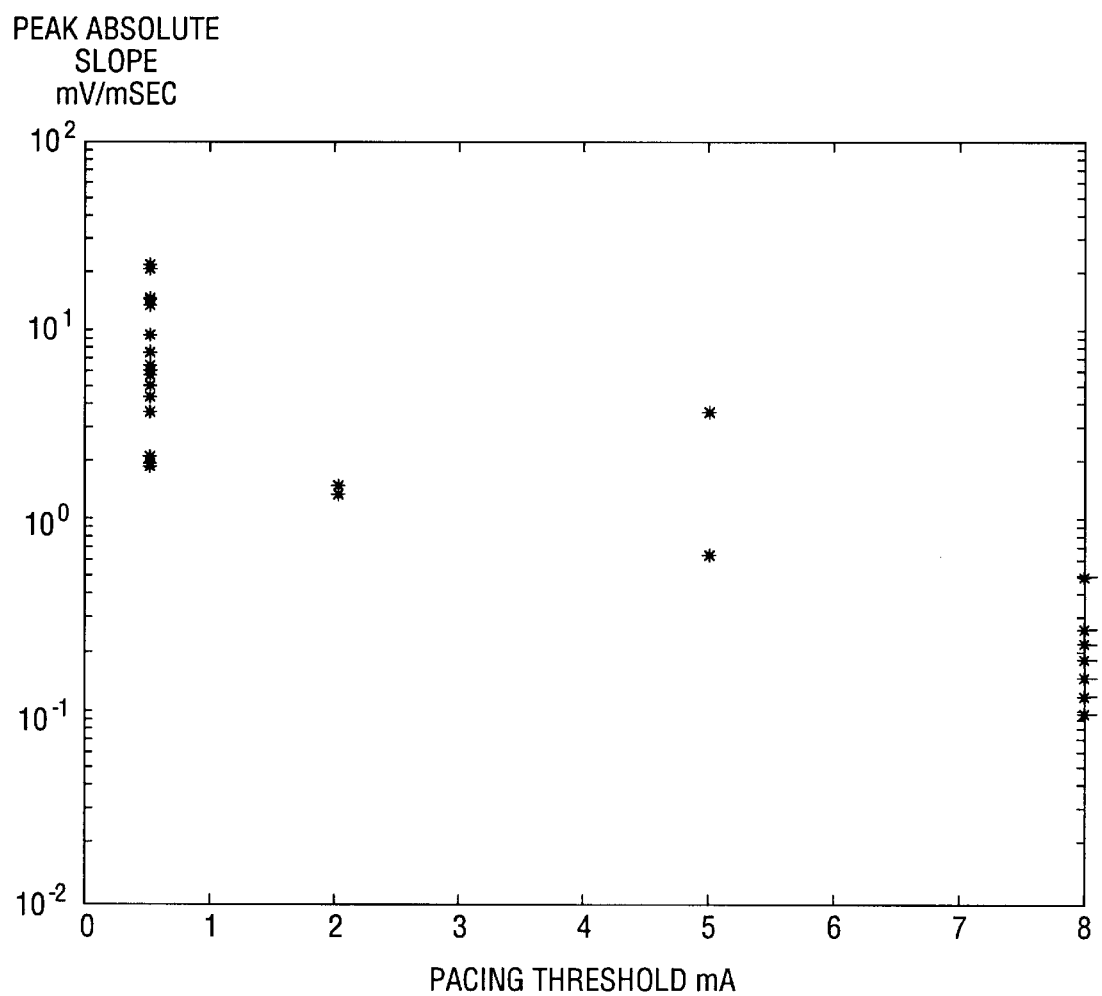

In order to verify that electrode contact can be estimated by calculating the absolute value of the slope of bipolar electrograms, two data sets were analyzed to find an initial range of output values and contact thresholds. The first data set was recorded during ventricular tachycardia from an electrode basket inserted in a human left ventricle, shown in FIG. 8. The other data set was recorded from a sheep during sinus rhythm using an electrode basket inserted in the right atrium, shown in FIG. 9. In FIGS. 8 and 9, the log of the peak absolute slope is plotted against pacing thresholds for the two data sets. For simplicity, the bipoles that did not pace are plotted with a pacing threshold of 8 mA, and so true pacing thresholds were not measured for these points. Pacing was performed at fixed outputs of 2 and 5 mA for the human data shown in FIG. 8, and pacing was performed at fixed outputs of 0.5, 2, and 5 mA for the sheep data shown in FIG. 9.

As can be seen in FIGS. 8 and 9, there is a strong correlation between the peak absolute slope and pacing thresholds, i.e., as pacing threshold increases, the peak absolute slope decreases. Furthermore, the two data sets taken from different models in different chambers and different rhythms exhibit similar thresholds for contact and no contact based on pacing thresholds. Therefore, if pacing thresholds can be correlated with electrode contact, peak absolute slope can be correlated with electrode contact as well.

Using pacing thresholds as a criteria for contact, the following thresholds can be set: 1) the electrodes are in contact when the pacing thresholds are less than 2 mA; 2) the quality of contact is unknown when the pacing thresholds are about 5 mA; and 3) the electrodes are not in contact when the pacing thresholds are greater than 5 mA. Using these thresholds, the bipoles in contact have a peak absolute slope in the range of 1 to 30 mV/ms, and those bipoles not in contact have a peak absolute slope in the range of 0.1 to 1 mV/ms. Therefore, a reasonable range of output values which covers bipoles in contact and not in contact is 0.1 to 10 mV/ms, and a log scale tends to better represent the slope data than a linear scale.

Figure 10:
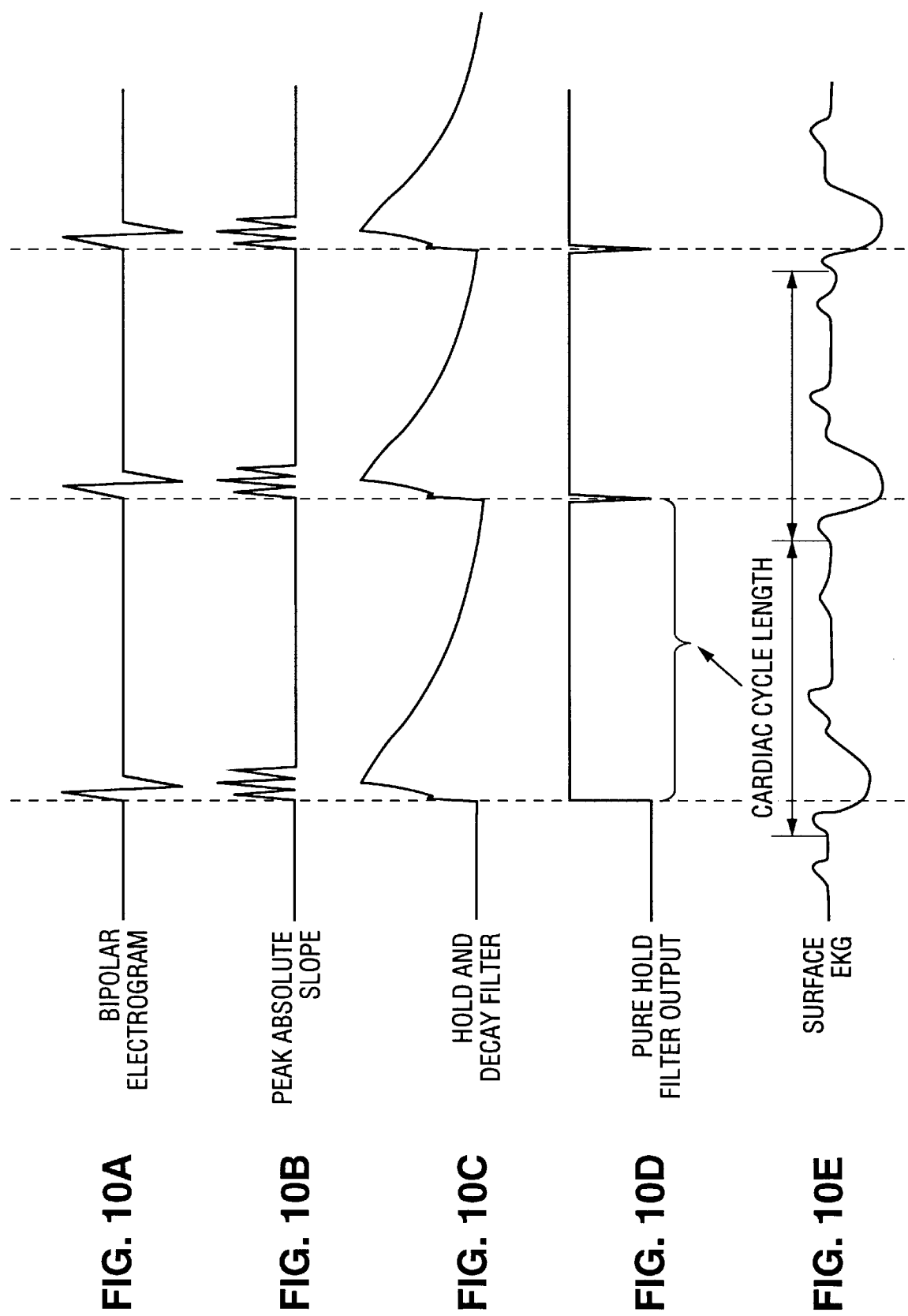
FIGS. 10A through 10E are plots of an EGM signal, its peak absolute slope, two different filters, and a surface EKG signal, respectively.

Referring back to FIG. 4, the computer 38 calculates the absolute slope of each in-coming EGM signal. For example, FIG. 10A is a plot of a single bipolar EGM signal, and FIG. 10B is a plot of its peak absolute slope. As can be seen, each activation in the EGM signal creates a pulse in the peak absolute slope. The amplitude of the pulse in the peak absolute slope is proportional to the degree of electrode contact.

Figure 11:
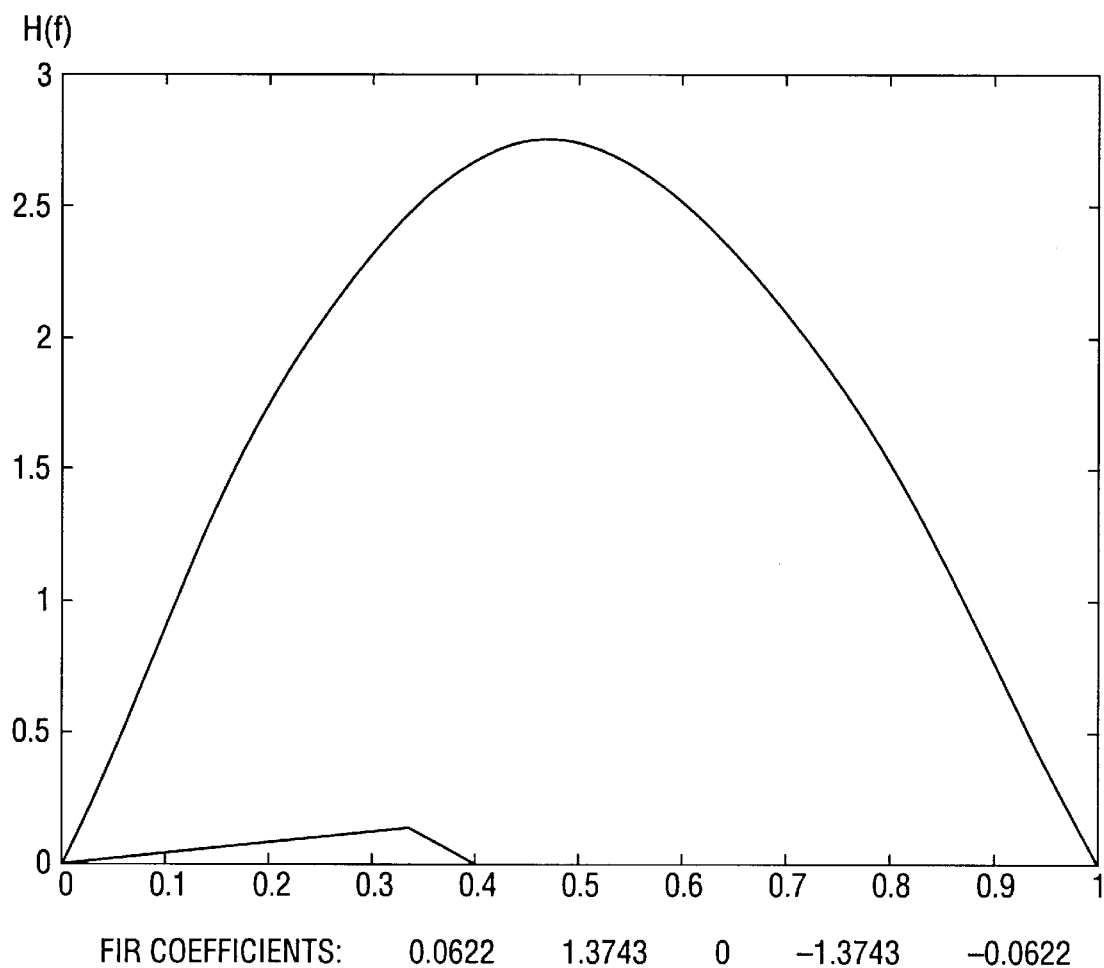
FIG. 11 is a frequency response plot of a finite input response (FIR) filter.

The computer 38 calculates the absolute slope of each in-coming EGM signal by executing slope calculation software. Specifically, the slope calculation software may include software designed to implement a finite input response (FIR) filter. Such an FIR filter may be designed using a Remez exchange algorithm followed by a Hanning window. These algorithms are implemented in many commercially available software packages such as Matlab, available from The Mathworks, Inc., Natick, Mass. The frequency response of such an FIR filter is shown in FIG. 11. The length of the filter may be chosen to minimize the computational overhead of the slope calculation; for example, 4 taps provides such minimization. The filter taps may be normalized to give an output in V/ms.

After the absolute slope of each in-coming EGM signal is calculated, the computer 38 processes the slope information in order to present it in a form that can be quickly visualized and utilized by a clinician in real-time. One possible form in which to present the slope information is to display time waveforms of the absolute slope of each bipolar electrode in real-time. However, this form tends to be somewhat ineffective because it is too much information for the user to process, similar to the original EGM signals themselves.

Figure 12B:
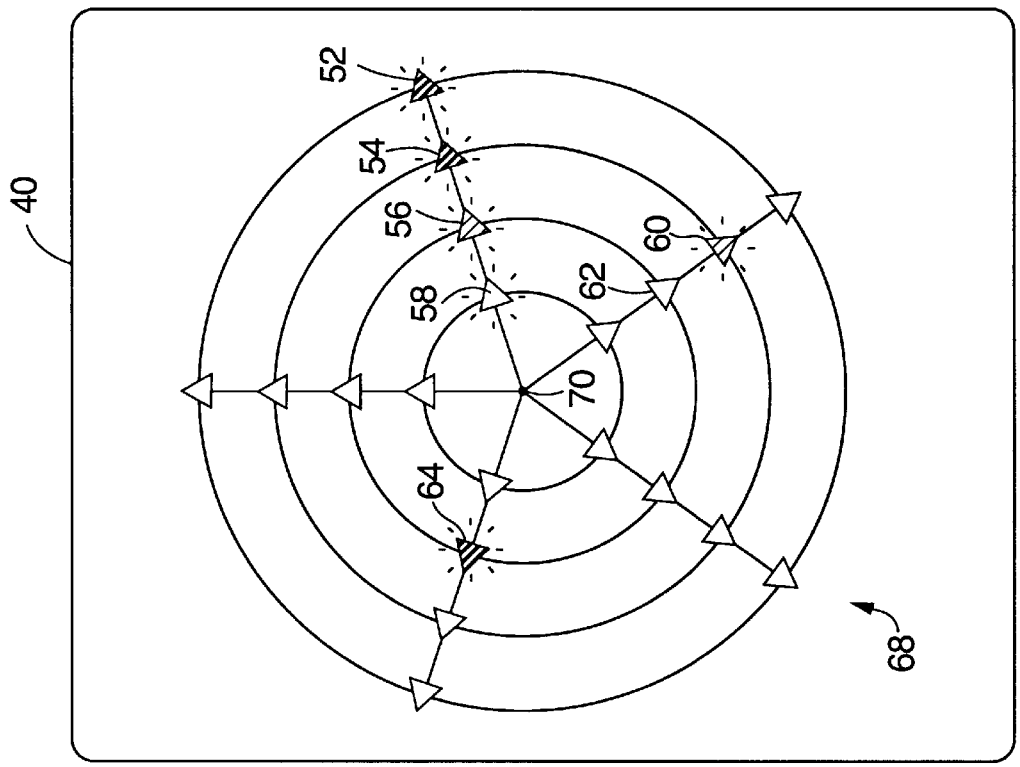
FIGS. 12A, 12B and 12C are video display images corresponding to various catheters.
Figure 12A:
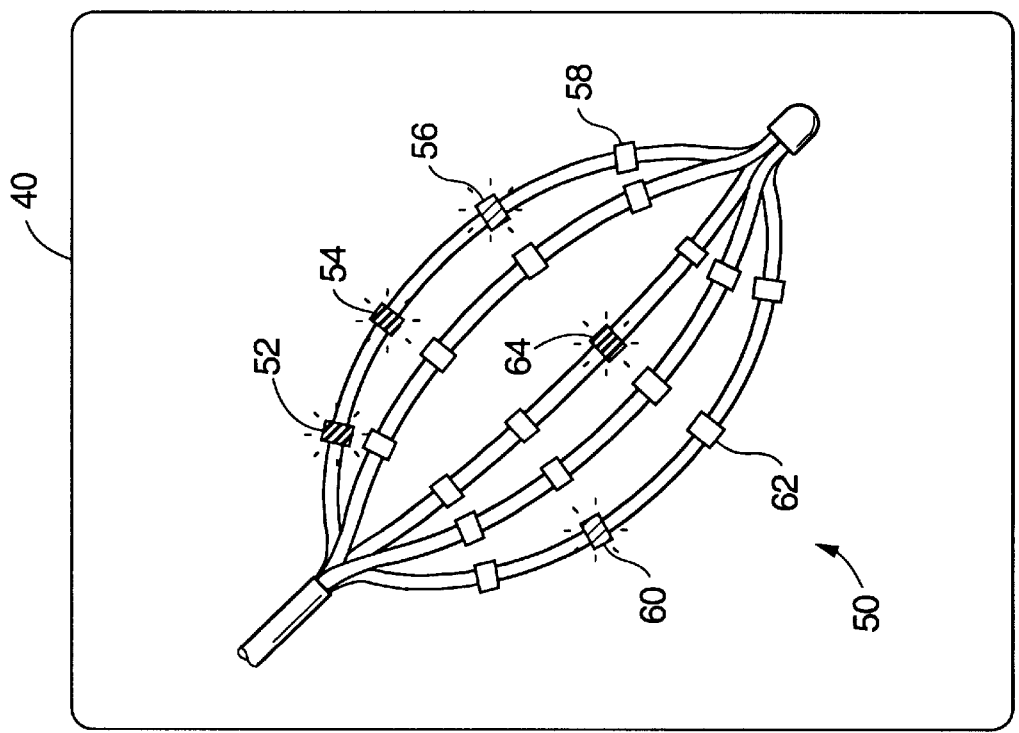
Figure 12C:
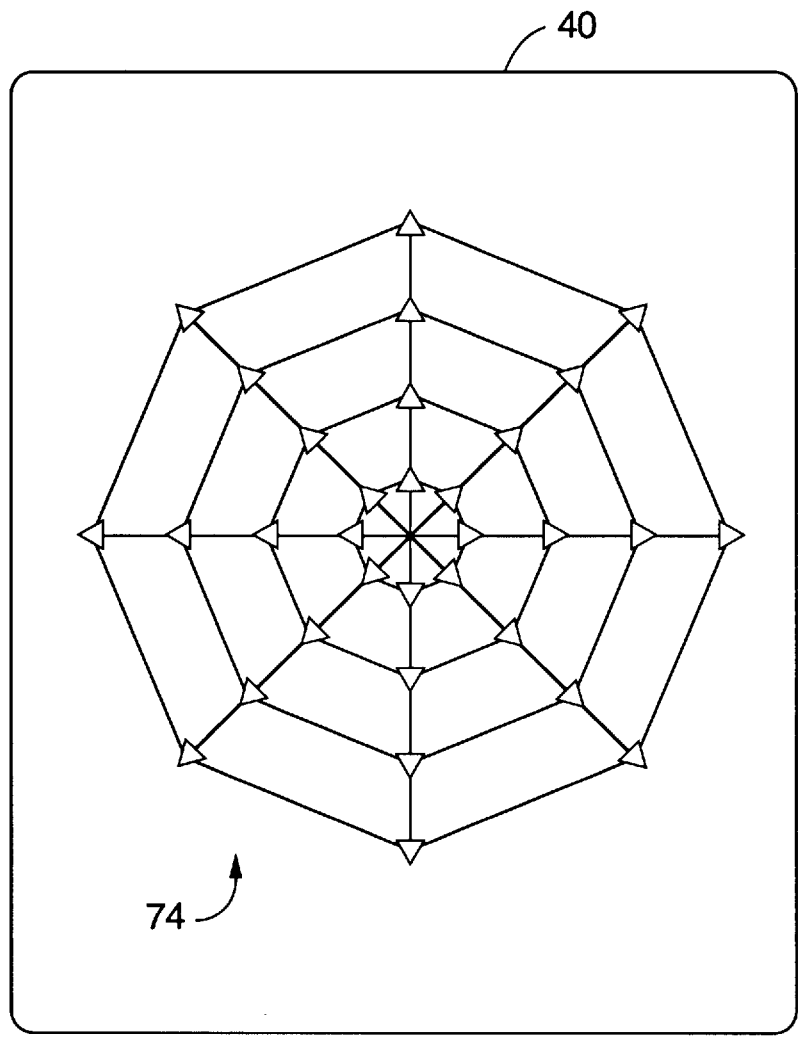

A better approach is to generate and display on the graphical display 40 the time varying absolute slope of each bipole as a first image, such as for example a dot or light, on a second image which corresponds to the catheter, as shown in FIGS. 12A, 12B and 12C. The first image corresponds to the respective electrode, either a bipole pair or unipole. The second image may be a depiction representative of the catheter. Specifically, FIG. 12A shows a three dimensional image 50 of the basket-shaped electrode array catheter 20 displayed on the graphical display 40. The catheter 50 includes such images as glowing lights or color dots, such as lights 52, 54, 56, 58, 60, 62, 64, each of which corresponds to a bipole on the catheter 20.

The computer 38 executes software, indicated by block 66 in FIG. 4, which adjusts either the intensity, brightness or color of the glowing lights in order to indicate the calculated degree of contact, e.g., absolute slope, for the EGM signal sensed by that specific bipole. For example, lights 52, 54, 64 are the brightest which may indicate that the corresponding EGM signals have very steep slopes, and thus, the corresponding bipoles, i.e., electrode pairs, on the catheter 20 are making very good contact with the endocardial surface.

Lights 56, 60 are less bright, indicating that the calculated slopes of the corresponding EGM signals are lower, or less steep, and thus, the corresponding bipoles on the catheter 20 are not in full contact with the endocardial surface. Finally, lights 58, 60, as well as the remainder of the lights, are either very dim or not glowing at all, indicating that the slopes of the corresponding EGM signals are very gentle, and thus, the corresponding bipoles on the catheter 20 are making either very weak contact, or no contact, with the endocardial surface. In this example, the intensity of the lights is proportional to the degree of contact. However, it should be understood that the computer 38 may adjust the visual appearance of the lights, or dots, in many different ways in accordance with the present invention. As another example, the blink rate, or even the size, of the glowing lights may be adjusted in order to indicate the calculated degree of contact. The blink rate could be increased, or the size of the lights could be increased, for bipoles that are in contact.

It should be well understood that the image of the catheter 20, or whatever catheter is used, may be generated in whatever form the user finds most easy to visualize and understand. For example, although FIG. 12A basically shows a three dimensional "picture" of the catheter 20, FIG. 12B shows an alternative two dimensional image 68 of the catheter 20. Specifically, the graphical representation 68 shows the five arms 22 of the catheter 20 spread out flat with the tip 23 of the catheter 20 corresponding to the center 70 of the graphical representation 68. The lights 52, 54, 56, 58, 60, 62, 64 shown in FIG. 12A have been labeled in FIG. 12B. The lights glow with varying intensities as described above to indicate the calculated absolute slope for the EGM signal sensed by the corresponding bipole. Some users find the image 68 shown in FIG. 12B easier to use than the image 50 shown in FIG. 12A. As another example, FIG. 12C shows an image 74 of a high density, full chamber mapping basket which includes eight arms and 32 bipoles.

As can be seen in FIG. 10B, the calculated peak absolute slope changes very quickly; i.e., the slope changes from zero to maximum, and back to zero very quickly. If the intensity, brightness or color of the glowing lights shown in FIGS. 12A, 12B and 12C corresponded directly to the calculated slope of each EGM signal, the lights would turn on and off or change colors very quickly, making it difficult for the user to comprehend the information provided by each light. This is because the portion of the EGM signal which contains the steepest slope is very short in duration, i.e., only 10–50 ms long. This portion would produce a very short duration flash of high intensity color that would not register with the user.

In order to avoid the problem of the lights turning on and off too quickly, the computer 38 executes software designed to function as a max hold and decay filter 72 before the calculated slopes are displayed as glowing lights on the video display 40. The hold and decay filter 72 holds the peaks in the calculated absolute slopes long enough so that they can be visualized by the user. This is accomplished by implementing the following state equation in the hold and decay filter 72:

$$y_{n+1} = \max(x_{n+1}, \alpha y_n) \quad y_0 = 0 \qquad (\text{EQ. 1})$$

where $x_n$ is the input sequence, $y_n$ is the output sequence and $\alpha$ is a parameter which controls the amount of decay. If $\tau$ is the desired time constant of the decay and T is the sampling period of the input data, then $\alpha$ is chosen using the following equation:

$$\alpha = 10^{\frac{-0.3T}{\tau}} \quad \text{(EQ 2)}$$

Figure 13:
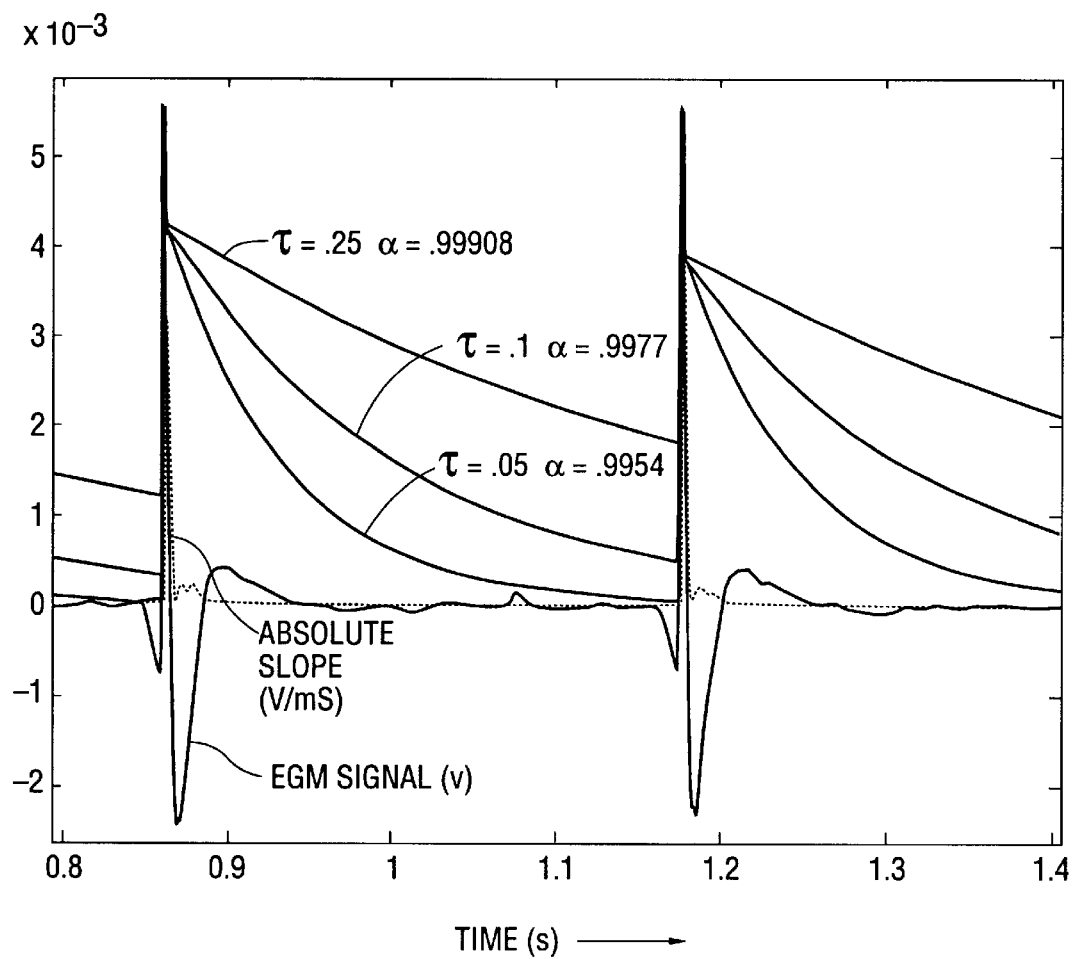
FIG. 13 is a plot illustrating the effect of a hold and decay filter in accordance with the present invention on the peak slope of a typical EGM signal.

The hold and decay filter 72 blurs or spreads out the peaks in the calculated absolute slope so that they are visible to the user. The amount of blurring is controlled by the a parameter. FIG. 13 shows the effect of the hold and decay filter 72 on the peak slope of a typical cardiac electrogram (EGM) for several different decay time constants $\tau$, i.e., several different values for the decay parameter $\alpha$. As can be seen, the hold and decay filter will cause the lights on the catheter images shown in FIGS. 12A, 12B and 12C to slowly go dim rather than shut off very quickly.

As mentioned above, there is no loss of information by taking the absolute value of the slope. Therefore, the algorithm can be written in equation form as:

$$y_{n+1} = \max(abs(b_{n+1}), \alpha y_n) y_0 = 0 \quad \text{(EQ. 3)}$$

$b_n$ is the first temporal derivative of the recorded bipolar signal and $y_n$ is the algorithm output. FIG. 10C shows the effect of the hold and decay filter 72 on the peak absolute slope shown in FIG. 10B. Each pulse in the peak absolute slope causes a step function followed by a slow-decay in the output of the hold and decay filter 72.

It should be understood that the hold and decay filter is only one technique for delaying the peaks of the absolute slope signal long enough for the user to visualize them. For example, the absolute slope signal could be passed through a filter which detects peaks and holds them as a constant value for a specific time interval after which the output is set to a value corresponding to no contact. The time interval could be set to the length of the patient's cardiac cycle. This cardiac cycle length could be calculated from a surface electrogram signal using a QRS detection algorithm. These algorithms are commonly used to determine the cardiac rate (i.e., inverse of the cardiac cycle length) for patient monitoring systems. FIG. 10D shows the output of this pure hold technique for a typical bipolar electrogram. As another example, the absolute slope signal could be passed through an infinite impulse response (IIR) filter which gives an output similar to the hold and decay filter 72.

Figure 14:
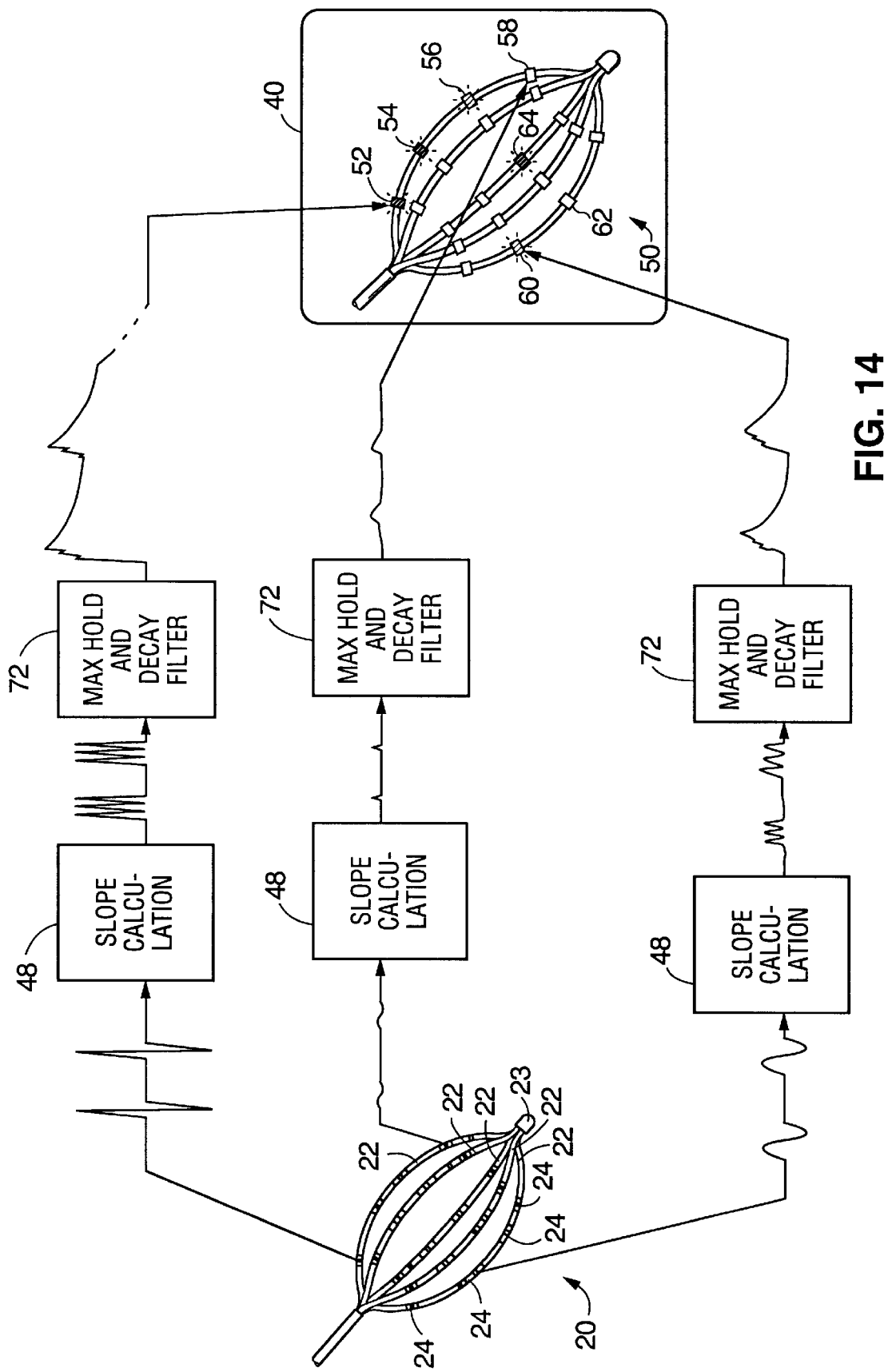
FIG. 14 is a block diagram illustrating the operation of the system shown in FIG. 4.

FIG. 14 summarizes the above discussion. The EGM signal sensed by each basket bipole is processed by the peak absolute slope software 48, followed by the hold and decay filter 72. The resulting signals are then displayed on the image 50 of the catheter 20 on the video display 40. The catheter bipoles are represented on the image 50 as glowing lights and the brightness or color of each light corresponds to the output of the hold and decay filter 72. The purpose of the hold and decay filter 72 is to blur or extend the pulses in the peak absolute slope signal long enough for the user to see them in the graphical display.

As can be seen, light 52 is bright because of the large spikes at the output of the slope calculation block 48. This indicates that the corresponding bipoles on the catheter 20 are making good contact with the endocardial surface. On the other hand, light 60 is not as bright, indicating less contact, and light 58 is dim (or off) indicating poor or no contact. The resulting display provides real-time contact information for each beat of the heart.

The computer 38 provides several functions. Specifically, it monitors the voltage potentials sensed by the catheter 20's electrodes on the tissue surface. It processes the voltage potentials in real time to calculate the degree of contact between each electrode and the tissue surface. The computer 38 also generates the graphics which are displayed on the video display 40 in real time. Such graphics include the graphical representation of the calculated degree of contact which is displayed on the image corresponding to the catheter 20.

An example of the graphical representation of the calculated degree of contact is a dot, corresponding to its respective electrode, positioned on the image corresponding to the catheter 20. The dot has a visual appearance which is altered by the computer 38 to indicate the calculated degree of contact. Again, the computer 38 may, for example, alter the visual appearance of the dot by adjusting the brightness of the dot or by changing the color of the dot.

If the degree of contact is determined by calculating the slope of the respective EGM signal, then the computer 38 generates a graphical representation of the calculated slope which is displayed on the image corresponding to the catheter 20. Furthermore, the computer 38 also executes software which filters the signal corresponding to the degree of contact according to a hold and decay function discussed above.

The catheter that is used with the system 30 will normally have at least one electrode. The electrodes may be arranged to function as single electrodes, i.e., unipoles, or they may be arranged to function in electrode pairs, i.e., bipoles. And again, the catheter may have any shape.

It has been found that the positioning information provided by the system 30 tends to be more accurate when the system 30 is used with catheters having platinum black electrodes versus catheters having gold electrodes. Specifically, it is believed that gold electrodes cause the resulting signals to have large artifacts on them whenever the user touches the catheter shaft. These artifacts have steep slope which create large artifacts in the contact display, resulting in incorrect feedback from the contact display during catheter handling. Platinum black electrodes, on the other hand, do not cause such artifacts because they tend to be much more immune to noise.

The system 30 allows the user to interact with the catheter 20 and receive immediate feedback from the contact display in real-time. The user can get the display to show good contact on all of the bipoles by inserting and holding the catheter 20 further in the apex. This will assist in getting the distal bipoles on all the arms, as well as all of the bipoles on a single arm, in contact.

It should be understood that various alternatives to the embodiments of the invention described herein may be employed in practicing the invention. It is intended that the following claims define the scope of the invention and that structures and methods within the scope of these claims and their equivalents be covered thereby.

What is claimed is:

1. A system for aiding in the positioning of a catheter against a surface of a tissue, the catheter having at least one electrode thereon, the system comprising:

monitoring means for monitoring a voltage potential generated by the tissue and sensed by the electrode;

processing means for processing the voltage potential to evaluate a degree of contact between the electrode and the surface of the tissue and for generating a contact signal representative of the degree of contact;

a video display; and graphics generation means, responsive to the contact signal, for generating and displaying on the video display a graphical representation of the degree of contact.

2. A system in accordance with claim 1, wherein the graphics generation means displays the graphical representation of the degree of contact on an image corresponding to the catheter.

3. A system in accordance with claim 1, wherein the graphical representation of the degree of contact comprises:

an image which corresponds to the electrode, the image having a visual appearance which is altered by the graphics generation means to indicate the degree of contact.

4. A system in accordance with claim 3, wherein the graphics generation means alters the visual appearance of the image by adjusting a brightness of the image.

5. A system in accordance with claim 3, wherein the graphics generation means alters the visual appearance of the image by changing a color of the image.

6. A system in accordance with claim 1, further comprising:

analog to digital conversion means for converting the sensed voltage potential to a digital signal.

7. A system for aiding in the positioning of a catheter against a tissue surface, the catheter having at least one electrode thereon, the system comprising:

monitoring means for monitoring a voltage potential sensed by the electrode on the tissue surface;

processing means for processing the voltage potential to evaluate a degree of contact between the electrode and the tissue surface and for generating a contact signal representative of the degree of contact;

a video display; and graphics generation means, responsive to the contact signal, for generating and displaying on the video display a graphical representation of the degree of contact;

wherein the processing means evaluates the degree of contact by calculating a rate of change of the sensed voltage potential.

8. A system for aiding in the positioning of a catheter against a tissue surface, the catheter having at least one electrode thereon, the system comprising:

monitoring means for monitoring a voltage potential sensed by the electrode on the tissue surface;

processing means for processing the voltage potential to evaluate a degree of contact between the electrode and the tissue surface and for generating a contact signal representative of the degree of contact;

a video display;

graphics generation means, responsive to the contact signal, for generating and displaying on the video display a graphical representation of the degree of contact; and filtering means for filtering the contact signal according to a hold and decay function.

9. A system for aiding in the positioning of a catheter, the system comprising:

a catheter having at least one electrode thereon for sensing a voltage potential generated by a tissue;

processing means for processing the voltage potential to evaluate a degree of contact between the electrode and the surface of the tissue and for generating a contact signal representative of the degree of contact;

a video display; and graphics generation means, responsive to the contact signal, for generating and displaying on the video display a graphical representation of the degree of contact.

10. A system in accordance with claim 9, wherein the catheter comprises:

a plurality of bipoles.

11. A system in accordance with claim 9, wherein the catheter comprises:

a basket shaped catheter which includes a plurality of electrodes.

12. A system in accordance with claim 9, wherein the graphics generation means displays the graphical representation of the degree of contact on an image corresponding to the catheter.

13. A system in accordance with claim 9, wherein the graphical representation of the degree of contact comprises:

an image which corresponds to the electrode, the image having a visual appearance which is altered by the graphics generation means to indicate the degree of contact.

14. A system in accordance with claim 13, wherein the graphics generation means alters the visual appearance of the image by adjusting a brightness of the image.

15. A system in accordance with claim 13, wherein the graphics generation means alters the visual appearance of the image by changing a color of the image.

16. A system for aiding in the positioning of a catheter, the system comprising:

a catheter having at least one electrode thereon for sensing a voltage potential on a tissue surface;

processing means for processing the voltage potential to evaluate a degree of contact between the electrode and the tissue surface and for generating a contact signal representative of the degree of contact;

a video display; and graphics generation means, responsive to the contact signal, for generating and displaying on the video display a graphical representation of the degree of contact;

wherein the processing means evaluates the degree of contact by calculating a rate of change of the sensed voltage potential.

17. A system for aiding in the positioning of a catheter, the system comprising:

a catheter having at least one electrode thereon for sensing a voltage potential on a tissue surface;

processing means for processing the voltage potential to evaluate a degree of contact between the electrode and the tissue surface and for generating a contact signal representative of the degree of contact;

a video display;

graphics generation means, responsive to the contact signal, for generating and displaying on the video display a graphical representation of the degree of contact; and filtering means for filtering the contact signal according to a hold and decay function.

18. A system for aiding in the positioning of a catheter, the system comprising:

a catheter having at least one electrode thereon for sensing a voltage potential generated by a tissue;

a video display; and a computer, coupled to the catheter and to the video display, which is programmed to process the voltage potential to evaluate a degree of contact between the electrode and a surface of the tissue and which is programmed to generate and display on the video display a graphical representation of the degree of contact on a first image corresponding to the catheter.

19. A system in accordance with claim 18, wherein the catheter comprises:
  a plurality of bipoles.

20. A system in accordance with claim 18, wherein the catheter comprises:
  a basket shaped catheter which includes a plurality of electrodes.

21. A system in accordance with claim 18, wherein the graphical representation of the degree of contact comprises:
  a second image positioned on the first image to correspond to the electrode, the second image having a visual appearance which is altered by the computer to indicate the degree of contact.

22. A system in accordance with claim 21, wherein the computer alters the visual appearance of the second image by adjusting a brightness of the second image.

23. A system in accordance with claim 21, wherein the computer alters the visual appearance of the second image by changing a color of the second image.

24. A system for aiding in the positioning of a catheter, the system comprising:
  a catheter having at least one electrode thereon for sensing a voltage potential on a tissue surface;
  a video display; and
  a computer, coupled to the catheter and to the video display, which is programmed to process the voltage potential to evaluate a degree of contact between the electrode and the tissue surface and which is programmed to generate and display on the video display a graphical representation of the degree of contact on a first image corresponding to the catheter;
  wherein the computer is programmed to calculate a slope of the voltage potential in evaluating the degree of contact between the electrode and the tissue surface.

25. A system for aiding in the positioning of a catheter, the system comprising:
  a catheter having at least one electrode thereon for sensing a voltage potential on a tissue surface;
  a video display; and
  a computer, coupled to the catheter and to the video display, which is programmed to process the voltage potential to evaluate a degree of contact between the electrode and the tissue surface and which is programmed to generate and display on the video display a graphical representation of the degree of contact on a first image corresponding to the catheter;
  wherein the computer is programmed to perform a hold and decay filtering function on the evaluated degree of contact.

26. A system for aiding in the positioning of a catheter, the system comprising:
  a basket shaped catheter having a plurality of bipoles arranged thereon for sensing voltage potentials on a tissue surface;
  an analog to digital converter coupled to the catheter and configured to convert the sensed voltage potentials to digital signals;
  a video display; and
  a computer, coupled to the analog to digital converter and to the video display, which is programmed to calculate an absolute value of a slope of each of the digital signals and which is programmed to generate and display on the video display a graphical representation of the absolute values of the slopes on a first image corresponding to the catheter.

27. A system in accordance with claim 26, wherein the computer is programmed to perform a hold and decay filtering function on each of the calculated slopes.

28. A system in accordance with claim 26, wherein the graphical representation of the calculated slopes comprises:
  a plurality of second images positioned on the first image so that each of the second images corresponds to a different one of the bipoles, the second images having a visual appearance which is altered by the computer to indicate a magnitude of the calculated slope.

29. A system in accordance with claim 28, wherein the computer alters the visual appearance of the second images by adjusting a brightness of each of the second images.

30. A system in accordance with claim 28, wherein the computer alters the visual appearance of the second images by changing a color of each of the second images.

31. A method for aiding in the positioning of a catheter against a surface of a tissue, the catheter having at least one electrode thereon, the method comprising the steps of:
  monitoring a voltage potential generated by the tissue and sensed by the electrode;
  processing the voltage potential to evaluate a degree of contact between the electrode and the surface of the tissue;
  generating a graphical representation of the degree of contact on a first image corresponding to the catheter; and
  displaying the graphical representation and the first image on a video display.

32. A method in accordance with claim 31, wherein the generating step comprises the steps of:
  positioning a second image on the first image to correspond to the electrode; and
  altering a visual appearance of the second image to indicate the degree of contact.

33. A method in accordance with claim 32, wherein the altering step comprises the step of:
  adjusting a brightness of the second image.

34. A method in accordance with claim 32, wherein the altering step comprises the step of:
  changing a color of the second image.

35. A method in accordance with claim 31, further comprising the step of:
  converting the sensed voltage potential to a digital signal.

36. A method for aiding in the positioning of a catheter against a tissue surface, the catheter having at least one electrode thereon, the method comprising the steps of:
  monitoring a voltage potential sensed on the tissue surface by the electrode;
  processing the voltage potential to evaluate a degree of contact between the electrode and the tissue surface by calculating a slop of the sensed voltage potential;
  generating a graphical representation of the degree of contact on a first image corresponding to the catheter; and
  displaying the graphical representation and the first image on a video display.

37. A method for aiding in the positioning of a catheter against a tissue surface, the catheter having at least one electrode thereon, the method comprising the steps of:
  monitoring a voltage potential sensed on the tissue surface by the electrode;
  processing the voltage potential to evaluate a degree of contact between the electrode and the tissue surface;

filtering the evaluated degree of contact according to a hold and decay function;

generating a graphical representation of the degree of contact on a first image corresponding to the catheter; and displaying the graphical representation and the first image on a video display.

38. A method for aiding in the positioning of a catheter against a surface of a tissue, the method comprising the steps of:

sensing a voltage potential generated by the tissue with a catheter having at least one electrode thereon;

processing the voltage potential to evaluate a degree of contact between the electrode and the surface of the tissue;

generating a graphical representation of the degree of contact on a first image corresponding to the catheter; and displaying the graphical representation and the first image on a video display.

39. A method in accordance with claim 38, wherein the sensing step comprises the step of:

sensing the voltage potential with a catheter having a plurality of bipoles thereon.

40. A method in accordance with claim 38, wherein the sensing step comprises the step of:

sensing the voltage potential with a basket shaped catheter which includes a plurality of electrodes.

41. A method in accordance with claim 38, wherein the generating step comprises the steps of:

positioning a second image on the first image to correspond to the electrode; and altering a visual appearance of the second image to indicate the calculated degree of contact.

42. A method in accordance with claim 41, wherein the altering step comprises the step of:

adjusting a brightness of the second image.

43. A method in accordance with claim 41, wherein the altering step comprises the step of:

changing a color of the second image.

44. A method for aiding in the positioning of a catheter against a tissue surface, the method comprising the steps of:

sensing a voltage potential on a tissue surface with a catheter having at least one electrode thereon;

processing the voltage potential to evaluate a degree of contact between the electrode and the tissue surface by calculating a slope of the sensed voltage potential;

generating a graphical representation of the degree of contact on a first image corresponding to the catheter; and displaying the graphical representation and the first image on a video display.

45. A method for aiding in the positioning of a catheter against a tissue surface, the method comprising the steps of:

sensing a voltage potential on a tissue surface with a catheter having at least one electrode thereon;

processing the voltage potential to evaluate a degree of contact between the electrode and the tissue surface;

filtering the evaluated degree of contact according to a hold and decay function;

generating a graphical representation of the degree of contact on a first image corresponding to the catheter; and displaying the graphical representation and the first image on a video display.

46. A system for aiding in the positioning of a catheter against a tissue surface, the catheter having at least one electrode thereon, the system comprising:

monitoring means for monitoring a voltage potential sensed by the electrode;

processing means for processing the voltage potential to evaluate a degree of contact between the electrode and the tissue surface and for generating a contact signal representative of the degree of contact;

a video display; and graphics generation means, responsive to the contact signal, for generating and displaying on the video display a graphical representation of the degree of contact;

wherein the processing means evaluates the degree of contact by calculating a rate of change of the sensed voltage potential.

47. A system for aiding in the positioning of a catheter against a tissue surface, the catheter having at least one electrode thereon, the system comprising:

monitoring means for monitoring a voltage potential sensed by the electrode;

processing means for processing the voltage potential to evaluate a degree of contact between the electrode and the tissue surface and for generating a contact signal representative of the degree of contact;

a video display;

graphics generation means, responsive to the contact signal, for generating and displaying on the video display a graphical representation of the degree of contact; and filtering means for filtering the contact signal according to a hold and decay function.

48. A system for aiding in the positioning of a catheter, the system comprising:

a catheter having at least one electrode thereon for sensing a voltage potential;

processing means for processing the voltage potential to evaluate a degree of contact between the electrode and the tissue surface and for generating a contact signal representative of the degree of contact;

a video display; and graphics generation means, responsive to the contact signal, for generating and displaying on the video display a graphical representation of the degree of contact;

wherein the processing means evaluates the degree of contact by calculating a rate of change of the sensed voltage potential.

49. A system for aiding in the positioning of a catheter, the system comprising:

a catheter having at least one electrode thereon for sensing a voltage potential;

processing means for processing the voltage potential to evaluate a degree of contact between the electrode and the tissue surface and for generating a contact signal representative of the degree of contact;

a video display;

graphics generation means, responsive to the contact signal, for generating and displaying on the video display a graphical representation of the degree of contact; and filtering means for filtering the contact signal according to a hold and decay function.

50. A system for aiding in the positioning of a catheter, the system comprising:
a catheter having at least one electrode thereon for sensing a voltage potential;
a video display; and
a computer, coupled to the catheter and to the video display, which is programmed to process the voltage potential to evaluate a degree of contact between the electrode and a tissue surface and which is programmed to generate and display on the video display a graphical representation of the degree of contact on a first image corresponding to the catheter;
wherein the computer is programmed to calculate a slope of the voltage potential in evaluating the degree of contact between the electrode and the tissue surface.

51. A system for aiding in the positioning of a catheter, the system comprising:
a catheter having at least one electrode thereon for sensing a voltage potential;
a video display; and
a computer, coupled to the catheter and to the video display, which is programmed to process the voltage potential to evaluate a degree of contact between the electrode and a tissue surface and which is programmed to generate and display on the video display a graphical representation of the degree of contact on a first image corresponding to the catheter;
wherein the computer is programmed to perform a hold and decay filtering function on the evaluated degree of contact.

52. A system for aiding in the positioning of a catheter, the system comprising:
a basket shaped catheter having a plurality of bipoles arranged thereon for sensing voltage potentials;
an analog to digital converter coupled to the catheter and configured to convert the sensed voltage potentials to digital signals;
a video display; and
a computer, coupled to the analog to digital converter and to the video display, which is programmed to calculate an absolute value of a slope of each of the digital signals and which is programmed to generate and display on the video display a graphical representation of the absolute values of the slopes on a first image corresponding to the catheter.

53. A system in accordance with claim 52, wherein the computer is programmed to perform a hold and decay filtering function on each of the calculated slopes.

54. A system in accordance with claim 52, wherein the graphical representation of the calculated slopes comprises:
a plurality of second images positioned on the first image so that each of the second images corresponds to a different one of the bipoles, the second images having a visual appearance which is altered by the computer to indicate a magnitude of the calculated slope.

55. A system in accordance with claim 54, wherein the computer alters the visual appearance of the second images by adjusting a brightness of each of the second images.

56. A system in accordance with claim 54, wherein the computer alters the visual appearance of the second images by changing a color of each of the second images.

57. A method of aiding in the positioning of a catheter against a tissue surface, the catheter having at least one electrode thereon, the method comprising the steps of:
monitoring a voltage potential sensed by the electrode;
processing the voltage potential to evaluate a degree of contact between the electrode and the tissue surface by calculating a slope of the sensed voltage potential;
generating a graphical representation of the degree of contact on a first image corresponding to the catheter; and
displaying the graphical representation and the first image on a video display.

58. A method of aiding in the positioning of a catheter against a tissue surface, the catheter having at least one electrode thereon, the method comprising the steps of:
monitoring a voltage potential sensed by the electrode;
processing the voltage potential to evaluate a degree of contact between the electrode and the tissue surface;
filtering the evaluated degree of contact according to a hold and decay function;
generating a graphical representation of the degree of contact on a first image corresponding to the catheter; and
displaying the graphical representation and the first image on a video display.

59. A method of aiding in the positioning of a catheter against a tissue surface, the method comprising the steps of:
sensing a voltage potential with a catheter having at least one electrode thereon;
processing the voltage potential to evaluate a degree of contact between the electrode and the tissue surface by calculating a slope of the sensed voltage potential;
generating a graphical representation of the degree of contact on a first image corresponding to the catheter; and
displaying the graphical representation and the first image on a video display.

60. A method of aiding in the positioning of a catheter against a tissue surface, the method comprising the steps of:
sensing a voltage potential with a catheter having at least one electrode thereon;
processing the voltage potential to evaluate a degree of contact between the electrode and the tissue surface;
filtering the evaluated degree of contact according to a hold and decay function;
generating a graphical representation of the degree of contact on a first image corresponding to the catheter; and
displaying the graphical representation and the first image on a video display.

* * * * *